(12) United States Patent  (10) Patent No.: US 7,662,116 B2
Ritchey  (45) Date of Patent: *Feb. 16, 2010

(54) COVER FOR PROTECTING INTRAVENOUS ENTRY SITE

(76) Inventor: Connie Ritchey, 956 Witthuhn Way, Lexington, KY (US) 40503

( * ) Notice: Subject to any disclaimer, the term of this patent is extended or adjusted under 35 U.S.C. 154(b) by 575 days.

This patent is subject to a terminal disclaimer.

(21) Appl. No.: 11/247,711

(22) Filed: Oct. 11, 2005

(65) Prior Publication Data

US 2006/0084904 A1 Apr. 20, 2006

Related U.S. Application Data

(60) Provisional application No. 60/618,351, filed on Oct. 14, 2004.

(51) Int. Cl.
*A61F 5/00* (2006.01)

(52) U.S. Cl. .......................................... 602/3; 128/856
(58) Field of Classification Search ................. 602/3–5, 602/8, 20–23, 79; 128/845, 846, 849, 856
See application file for complete search history.

(56) References Cited

U.S. PATENT DOCUMENTS

| 5,643,183 | A  | * | 7/1997 | Hill ................................. 602/3 |
| 6,276,364 | B1 | * | 8/2001 | Warner ........................ 128/846 |
| 6,342,031 | B1 | * | 1/2002 | Vaughan ........................ 482/55 |
| 6,916,301 | B1 | * | 7/2005 | Clare ............................. 602/3 |

* cited by examiner

*Primary Examiner*—Michael A. Brown
(74) *Attorney, Agent, or Firm*—Stockwell & Smedley, PSC.

(57) ABSTRACT

A cover for preventing wetness or contamination of an intravenous site is disclosed. The cover is manufactured in a variety of sizes and can fit on any extremity of the human body.

8 Claims, 3 Drawing Sheets

COVER FOR PROTECTING INTRAVENOUS ENTRY SITE

CROSS-REFERENCE TO RELATED APPLICATIONS

This application claims priority to U.S. Provisional Application No. 60/618,351, which was filed on Oct. 14, 2004.

FIELD OF THE INVENTION

This invention relates generally to intravenous (IV) sites, and more specifically to a cover which can assist in preventing such a site from getting wet or contaminated.

BACKGROUND OF THE INVENTION

Withdrawing and re-inserting an intravenous needle is both time-consuming and expensive. However, patients must also be bathed, and/or showered, including potentially in the area of the IV site. At present, bathing a patient's wound area can necessitate withdrawing and re-inserting an intravenous needle.

Patients also frequently have intermittent infusions for IV medications and the nurse converts the IV infusion to a heparin lock or saline lock for intermittent infusion. Like the above, it is desired to avoid having to re-stick the heparin lock or saline lock. Consequently, a means for addressing these problems is desired.

SUMMARY OF THE INVENTION

It is an object of the present invention to provide an easily-installable means for protecting an IV site. It is another object of the present invention to achieve the above in multiple sizes so that it may fit the various sizes of human extremities. These and other objects and advantages of the invention will become readily apparent as the following description is read in conjunction with the accompanying drawings.

DETAILED DESCRIPTION OF THE PREFERRED EMBODIMENTS

Before explaining the disclosed embodiment of the present invention in detail it is to be understood that the invention is not limited in its application to the details of the particular arrangement shown, since the invention is capable of other embodiments. Also, the terminology used herein is for the purpose of description and not of limitation.

The present invention is directed toward a cover for protecting intravenous (IV) sites. It's expensive to restart an IV in terms of nurse time and also equipment. It can also be painful for the patient. Sometimes it takes multiple sticks to get it into a patient's arm or extremity and find the correct vein. Some hospitals have an intravenous starter kit that might use tape or gauze. However, these kits can be expensive. The entire kit includes a dressing which is sterilized and requires a nurse to wear non-latex gloves.

To continually reapply intravenous units requires a lot of nursing time. Also, if the injury or the wound, or the entry point of the IV is exposed, the sterility of the dressing may be at risk. This could lead to nosocomial infection, otherwise known as a hospital-acquired hospital-induced infection. Also, IV infections are much more serious than other types of infections, and can more quickly lead to septicimia. Sterile dressings can be either gauze, tegaderm, or other mechanisms.

Figure 2A:
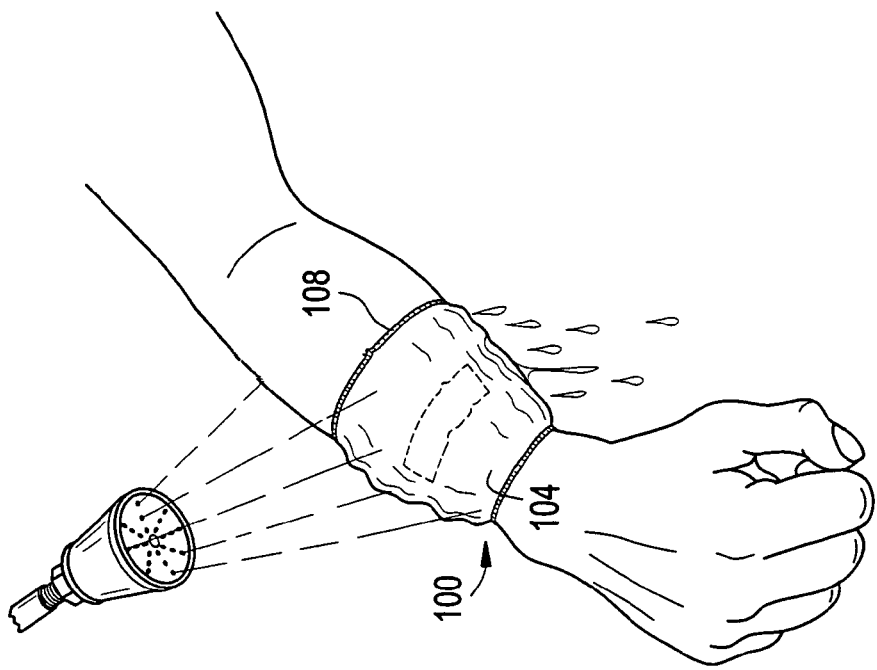
FIGS. 2A and 2B show an exemplary embodiment of the present invention protecting the IV site of FIG. 1 both disconnected (FIG. 2A) and connected (FIG. 2B) from a main IV line.
Figure 1:
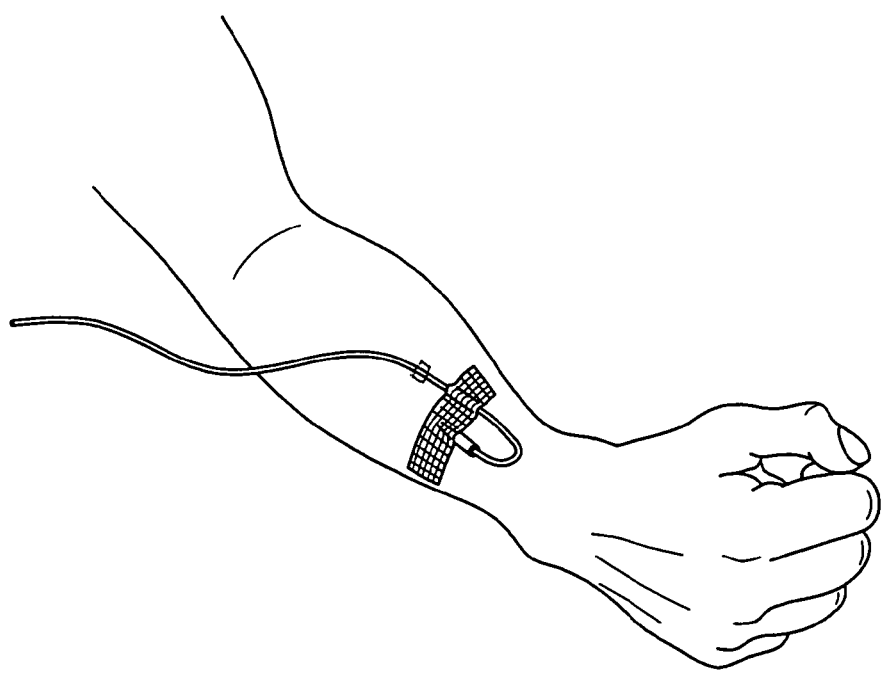
FIG. 1 shows an IV site on a forearm of a patient.
Figure 2B:
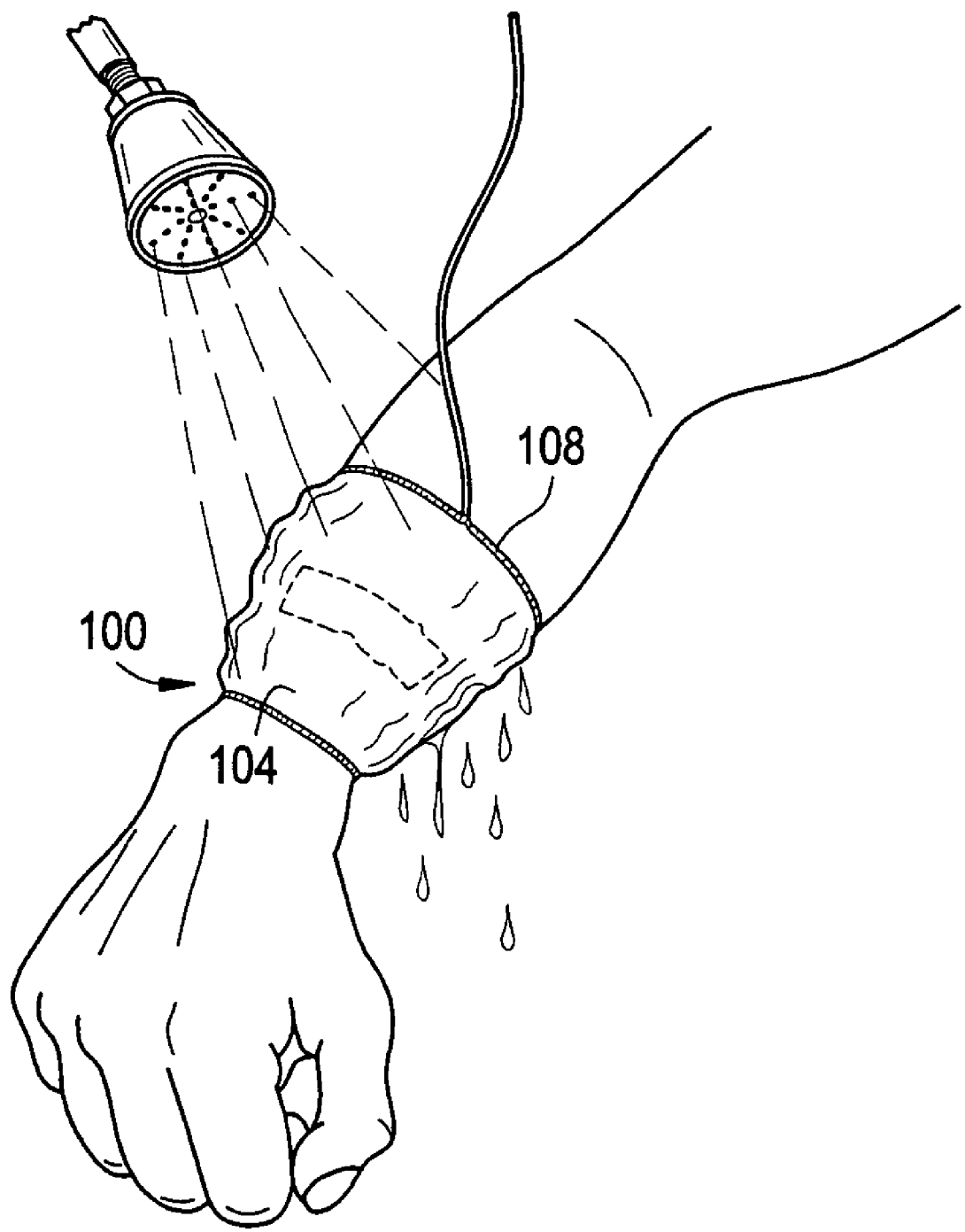

FIG. 1 shows an IV site on an upper right arm of a patient with a sterile dressing such as one of those discussed above. FIG. 2A shows an exemplary embodiment of the cover 100 of the present invention, positioned about the IV site of FIG. 1, where the IV site is disconnected from the main IV line. FIG. 2B shows the cover positioned about the IV site of FIG. 1, where the IV site remains connected to the main IV line.

The body 104 of the cover 100 can be made of the same type of plastic as shower caps, and is also waterproof. An exemplary embodiment could be made of low- or high-density polyethlene, although the present invention should not be considered as limited exclusively thereto.

It is important that the cover 104 be non-irritating to human skin. The cover 100 also comes equipped with elastic bands 108 molded or embedded within the cover 100, to assist in protecting the IV site. However, the elastic bands 108 do not grip so tightly that they interfere with the I.V. tubing. Thus, some water seepage is possible, so that even while using the present invention, it would still be necessary for a nurse and patient to exercise care with the showerhead. However, in the FIG. 2A embodiment where the IV tubing is temporarily disconnected, water seepage would be less of a problem, and potentially could be avoided altogether.

The cover 100 is only meant to reasonably prevent water or other substances from reaching the IV site. It is possible that under enough pressure or volume of water from a showerhead or other cleansing mechanism, some water could seep into the IV site. In such a case, the cover 100 could be removed, discarded, and replaced.

As shown in FIG. 2, the present invention wraps around the arm or other extremity of a wearer and is cylindrical in shape with elastic or clinging bands 108 at either end thereof. The cylinder of the body 104 is open-ended and slides over an IV site.

Figure 4:
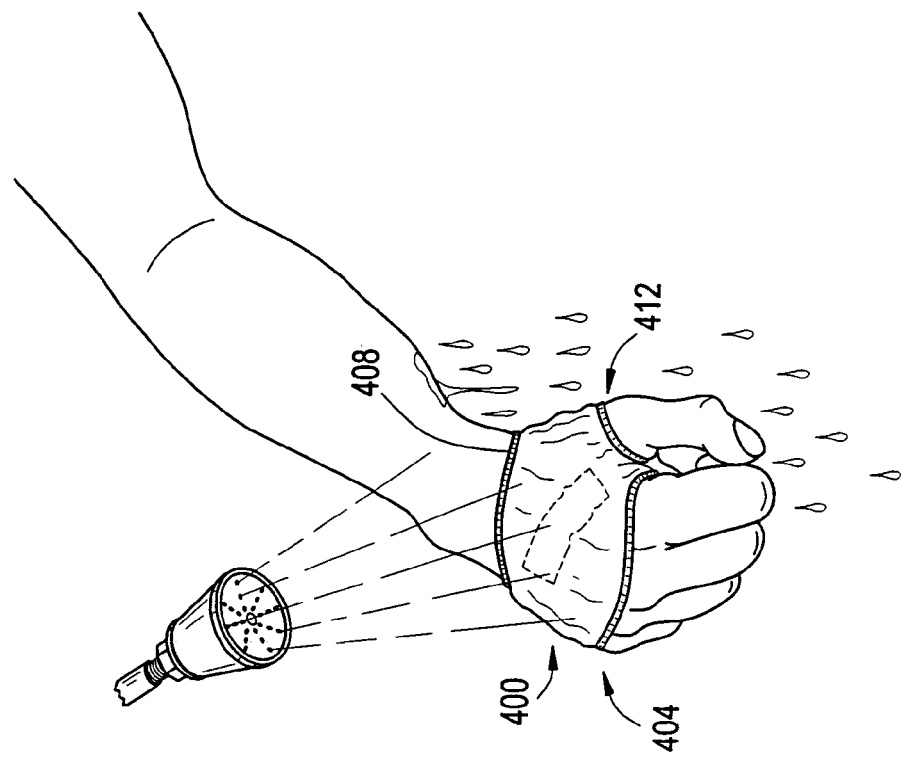
FIG. 4 shows a second embodiment of the present invention protecting the IV site of FIG. 3.
Figure 3:
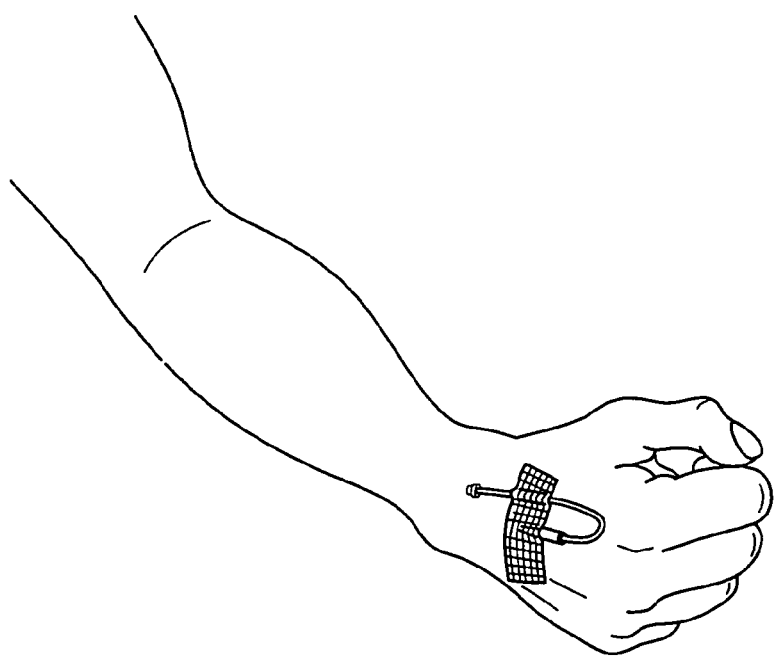
FIG. 3 shows an IV site on the wrist of a patient.

FIG. 3 shows another common location of an IV site, at the top of the right hand of a patient. FIG. 4 shows a second embodiment of the present invention, in which a cover 400 is not entirely cylindrical in shape, but has an extra hole for admitting a thumb so as to protect the IV site of FIG. 3. The cover 400 has a finger band 404, wrist band 408, and thumb band 412.

The present invention also contemplates other embodiments of the cover which could be adapted to fit other extremities where application of an IV is also suitable. One example of such an area is the upper leg. Additionally, the present invention could also be applied to peripheral intercannula catheters (PICs). Furthermore, the present invention could also be applied to other types of non-IV sites that need protection, such as stitches or sutures.

The body 104 of the cover 100 can also be made of nitrile latex, although other compositions are contemplated within the spirit and scope of the present invention. Other substances could include a durable semi-permeable membrane in which the molecules are 3 or 4 nanometers apart, such as Gore-Tex™.

Such a product could be manufactured by positioning a membrane gel, such as but not limited to a latex membrane, between slices of a loose-weave nylon formation layer and inserted in a baking or ceramic oven. The resulting combination of gel and nylon could then be heated to a specific temperature such as 300 F, with certain areas embedded with a heat-sensitive stripe of sealant that will bind all materials touching the sealant into a type of seam. However, the present invention should not be considered as limited thereto.

After returning to room temperature, the product could be chopped into grids, with the sealant-areas providing what will eventually be the seams of the product. The chopping process could also include perforations which would be useful for a tear-off packaging implementation, but could also be completely separated by some other type of cutting process. The printed chopped sheets could then be gamma-radiated for sterilization purposes, because gamma rays have proven to be effective at killing existing bacteria, and discouraging their further growth. It is not required that the cover be manufactured with seams. Instead, it could also be fabricated with a high-stress elasticizing process.

The cover 100 could be manufactured like a trash-bag that comes printed flat on a roll, where the user then tears off a single unit, and then fingers it open, before inserting the extremity. The cover 100 could also come in a disposable, sanitary single use package.

It is anticipated that various changes may be made in the arrangement and operation of the system of the present invention without departing from the spirit and scope of the invention, as defined by the following claims.

What is claimed is:

1. A method of manufacturing a cover for protecting an intravenous site on a human extremity, comprising:
   positioning a membrane gel between slices of a loose-weave nylon formation layer;
   inserting said combination in a baking or ceramic oven;
   incorporating upper and lower bands; and
   heating said combination to a predetermined temperature.

2. The method of claim 1, wherein said predetermined temperature is 300° F.

3. The method of claim 1, further comprising:
   applying sealant at pre-determined locations within said combination to produce seams and/or folds.

4. The method of claim 1, further comprising:
   returning said combination to room temperature.

5. The method of claim 4, further comprising:
   chopping said combination into grids.

6. The method of claim 5, wherein said chopping step further comprises:
   forming perforations for a tear-off spooled packaging mode.

7. The method of claim 1, further comprising:
   gamma-radiating said combination, for sterilization purposes.

8. The method of claim 1, further comprising:
   high-stress elasticizing process.

* * * * *